United States Patent [19]

Wu et al.

[11] 4,246,177

[45] Jan. 20, 1981

[54] PREPARATION OF DIHYDROPYRANS

[75] Inventors: Yulin Wu; Ernest A. Zuech, both of Bartlesville, Okla.

[73] Assignee: Phillips Petroleum Company, Bartlesville, Okla.

[21] Appl. No.: 50,854

[22] Filed: Jun. 21, 1979

[51] Int. Cl.³ .......................................... C07D 309/18
[52] U.S. Cl. ................................................... 260/345.1
[58] Field of Search ...................... 260/345.1, 604 HF

[56] References Cited

U.S. PATENT DOCUMENTS

| 2,452,977 | 11/1948 | Williams et al. | 260/345.1 |
|---|---|---|---|
| 2,526,742 | 10/1950 | Gresham et al. | 260/586 |
| 2,648,694 | 8/1953 | Mason | 260/413 |
| 2,945,050 | 7/1960 | Franke et al. | 260/413 |
| 3,239,566 | 3/1966 | Slaugh et al. | 260/604 HF |
| 3,404,188 | 10/1968 | Privette et al. | 260/617 |
| 3,511,880 | 5/1970 | Booth | 260/604 HF |
| 3,527,809 | 9/1970 | Pruett et al. | 260/604 HF |
| 3,555,098 | 1/1971 | Olivier et al. | 260/604 HF |
| 3,560,539 | 2/1971 | Booth | 260/429 |
| 3,651,092 | 3/1972 | Stapp et al. | 260/345.1 |
| 3,725,305 | 4/1973 | Wilkinson | 252/429 R |
| 4,039,585 | 8/1977 | Homeier | 260/604 HF |
| 4,159,999 | 7/1979 | Stautzenberger et al. | 260/604 HF |

OTHER PUBLICATIONS

Kundo et al., Chemical Abstract, 69, 67677u, (1967).
Farberov et al., C. A., 55, 348b, (1961).
Stapp, Ind. Eng. Chem., Prod. Res. Dev., 15, 189, (1976).
Labutin et al., C. A., 56, 8872i, (1962).

Primary Examiner—Nicky Chan

[57] ABSTRACT

Dihydropyrans, such as 3,4-dihydro-4-methyl-2[H]-pyran, are prepared from unsaturated alcohols, such as 3-methyl-3-buten-1-ol, by reaction with carbon monoxide and hydrogen employing a Group VIII or VIB catalyst.

22 Claims, No Drawings

PREPARATION OF DIHYDROPYRANS

FIELD OF THE INVENTION

The invention pertains to the preparation of dihydropyrans.

BACKGROUND OF THE INVENTION

Dihydropyrans are potentially valuable chemicals. Yet, their potential remains largely unfilled due to lack of satisfactory commercially-viable methods of synthesis. Procedures for the synthesis of dihydropyrans have, for the most part, heretofore had the disadvantage of either giving modest yields, or using starting materials difficult to obtain, or both.

BRIEF SUMMARY OF THE INVENTION

We have discovered a new and useful method of producing dihydropyrans by the conversion of olefinically unsaturated aliphatic alcohols with carbon monoxide and hydrogen, in the presence of a suitable catalyst. The starting olefinic unsaturated alcohols are readily prepared from common chemicals by known methods, thus providing a distinct advantage of our method of preparing dihydropyrans.

DETAILED DESCRIPTION OF THE INVENTION

In accordance with our invention, dihydropyrans are prepared from β, γ monoolefinically unsaturated aliphatic hydrocarbyl alcohols (alkenols) in a reaction with carbon monoxide and hydrogen employing a catalyst under reaction conditions.

The olefinically unsaturated alcohols utilized in the process of our invention can be represented by formula I:

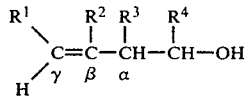 (I)

in which each of R¹, R², R³, and R⁴ is individually selected from hydrogen and lower alkyl radicals preferably of 1 to 6 carbon atoms per radical. The alcohols for suitable reactivity should not contain more than about 28 carbon atoms per molecule.

Presently preferred are unsaturated alcohols of formula I in which R¹, R³, and R⁴ are hydrogen, and R² is hydrogen or an alkyl radical of 1 to 4 carbon atoms as in formula II:

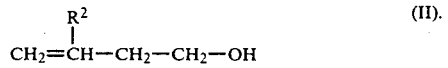 (II)

Examples of the unsaturated alcohols include 4-methyl-4-penten-2-ol, 2,3-dimethyl-3-buten-1-ol, 3-penten-1-ol, 3,4-dimethyl-4-penten-2-ol, 2-methyl-3-penten-1-ol, 3-methyl-3-buten-1-ol, 3-methylene-1-pentanol, 3-methylene-1-heptanol, 2-methyl-3-methylene-1-pentanol, and the like. For reasons of availability of the starting material and value of the resulting products the currently most preferred starting material for the process of this invention is 3-methyl-3-buten-1-ol:

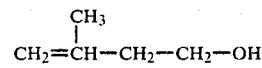 (III)

The unsaturated alcohols as starting materials for the process of our invention are readily prepared from aldehydes and olefins. For example, 3-methyl-3-buten-1-ol can be prepared from formaldehyde and isobutylene. The condensation of 1-butene with formaldehyde yields a cis/trans mixture of 3-penten-1-ol. A detailed discussion of this synthesis appears in 15 *IND. ENG. CHEM., PROD. RES. DEV.*, No. 3, 1976, pp. 189-192.

Catalysts

The catalysts utilized in the process of our invention are those generally recognized as suitable for oxo or hydroformylation reactions. Suitable catalysts include the elements or carbonyl compounds of the Group VIII and of Group VIB elements of the Periodic Table of the Elements. Examples of these metals include the preferred ruthenium, rhodium, palladium, platinum, and molybdenum, as well as chromium, tungsten, osmium, iridium, iron, cobalt, and nickel. Most preferred of these is rhodium. The amount of catalyst employed in our process can be expressed as a weight ratio of the metal (expressed as the element) to the unsaturated alcohol broadly of about 0.01/100 to 10/100, presently preferably about 0.05/100 to 5/100 since the lower level—to achieve satisfactory activity.

The catalyst frequently and preferably is utilized on a support although this is not required. Suitable supports include carbon, silica, alumina, molecular sieves, and the like, of which presently preferred is carbon for availability. Generally, the amount of catalyst on the support will range from about 0.1 to 20, preferably about 0.5 to 10, weight percent, based on the weight of the support alone.

Although not required, it is preferred that a trihydrocarbylphosphite promoter such as triphenylphosphite be present during the reaction, since it is believed to form in some cases more highly active catalytic species with the catalyst. The amount of the promoter generally will be in the range of about 0.05 to 50 weight percent, preferably in the range of about 0.01 to 20 weight percent as the most economically effective range, based on the weight of the alcohol reactant.

Reaction Conditions

The process of our invention employs a mixture of hydrogen and carbon monoxide. At least one mole of carbon monoxide and one mole of hydrogen per mole of starting unsaturated alcohol should be used, and generally a molar excess of carbon monoxide and hydrogen is advantageous. The relative proportions of hydrogen:carbon monoxide can vary widely, such as from about 1 to 99 mole percent hydrogen, presently preferably about 20 to 70 mole percent hydrogen since a 1:1 ratio is desired, and amounts of either in large excess are not needed, the balance being carbon monoxide.

The process of our invention preferably is carried out in a solvent that is substantially inert under the reaction conditions. Examples of suitable solvents include the glycols, such as ethylene glycol or propylene glycol; saturated alcohols, such as ethanol or 2-propanol; aromatics, such as benzene or toluene; and ethers, such as 1,4-dioxane or tetrahydrofuran; and mixtures. The amount of the solvent generally will range from about 20 to 2000 weight percent based on the weight of the starting alcohol.

The temperature utilized for the reaction should be that temperature effective for the particular reactants and catalyst. The temperature will depend on the specific catalyst used, but usually will be from about 0° C. to 200° C., preferably about 40° to 150° C.; below 0° is used only with some highly active catalyst or alkenol that is sensitive to higher temperature, and above 200° C. can be used when a less active catalyst is used.

The pressure utilized should be that pressure effective under the temperature used and for the specific catalyst and starting material chosen. The pressure generally will be from atmospheric pressure to about 1000 psig (6894 kiloPascals gauge—kPa). Since isomerization of the starting unsaturated alcohol sometimes can occur at the lower pressures, the preferred pressures are from about 75 (517 kPa) to 300 psig (2068 kPa).

The time employed for the reaction can vary over a wide range depending on the temperature, pressure, catalyst, and starting unsaturated alcohol. Generally, a time period from a few minutes to about 72 hours is suitable.

The reaction can be carried out batchwise, continuously, or intermittently, using any suitable method for contacting the unsaturated alcohol, hydrogen, carbon monoxide, and catalyst under conditions which cause the desired reaction to occur.

At the conclusion of the desired reaction time the product mixture can be worked up by any means known in the art. Gases can be vented, and, if desired, recycled. Generally, the catalyst or catalyst residues are separated from the reaction mixture by, for example, filtration, and the filtrate then is subjected to fractional distillation. Recovered solvent and unreacted unsaturated alcohol can be recycled to the reaction zone if desired.

Dihydropyran Product

The products of the preparation of our invention are dihydropyrans represented by formula IV:

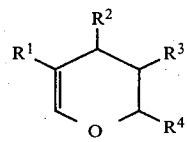
(IV)

in which each of $R^1$, $R^2$, $R^3$, and $R^4$ is as defined above. These products are 3,4-dihydro-2[H]-pyrans.

The product from the reaction of the currently preferred starting material (II) is represented by formula V:

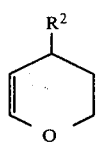
(V)

in which $R^2$ is as described above. This product is a 3,4-dihydro-4-alkyl-2[H]-pyran.

The product of the currently most preferred starting material (III) is 3,4-dihydro-4-methyl-2[H]-pyran represented by formula VI:

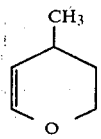
(VI)

The dihydropyran products of the process of our invention are useful as solvents for such as shellac and polymers. They also are useful as precursors for other valuable chemical compounds useful as lubricants, molding materials, and adhesives.

EXAMPLES

Examples provided are intended to assist one skilled in the art to a further understanding of the invention. Particular materials employed, relationships, proportions, species, conditions, and the like, are intended to be illustrative of our invention and not limitative of the reasonable scope thereof.

The chemicals and catalyst used in the examples were commercial materials and were not purified further before use. The results in the examples are area percents from gas-liquid chromatographic (glc) analysis and are not corrected for response factors.

EXAMPLE I

A 100 ml Fischer-Porter aerosol compatibility bottle equipped with a pressure gauge and magnetic stirrer was charged with 5 g (58 moles) of 3-methyl-3-buten-1-ol, 10 g of tetrahydrofuran, 0.5 g of triphenylphosphite, and 0.5 g of a rhodium on carbon catalyst (5 weight percent rhodium based on the weight of the support).

The reaction vessel was purged several times with hydrogen and then was purged with a mixture containing a 1:1 mole ratio (based on pressure) of carbon monoxide and hydrogen. The reaction vessel then was pressured to 50 psig (345 kPa) with a 1:1 mole ratio mixture of carbon monoxide and hydrogen, and heated to 75° C. The reaction mixture was stirred at about 75° C. for 14.5 hours. During the reaction period, the reaction vessel was pressured intermittently at 1 to 2 hour intervals with the 1:1 mixture of carbon monoxide and hydrogen to a pressure of about 150 psig (1034 kPa).

At the conclusion of the reaction time, the reaction mixture was cooled and filtered. A gas-liquid chromatographic (glc) analysis of the filtrate showed that the main product of the reaction was 3,4-dihydro-4-methyl-2[H]-pyran. The conversion of the 3-methyl-3-buten-1-ol starting material was 73.5 percent and the selectivity to the pyran was 54 percent with the percent selectivity based on the amount of alcohol converted. The structure of the 3,4-dihydro-4-methyl-2[H]-pyran was established by mass spectroscopy and NMR spectroscopy.

The results of this run demonstrate the process of our invention for the conversion of unsaturated alcohols to dihydropyrans.

EXAMPLE II

A 100 ml Fischer-Porter aerosol compatibility bottle equipped with a pressure gauge and magnetic stirrer was charged with 10 g (116 mmoles) of 3-methyl-3-buten-1-ol, 20 g of tetrahydrofuran, 0.5 g of triphenylphosphite, and 0.5 g of a catalyst containing 5 weight percent rhodium on a carbon support. The reaction was carried out employing the same procedure as described above in Example I except that the reaction temperature was about 65° C., the reactor was pressured intermittently to about 70 psig (482 kPa) with a 1:1 mole ratio mixture of carbon monoxide and hydrogen, and the reaction time was 6.33 hours.

At the conclusion of the reaction time the reaction mixture was cooled, filtered, and the filtrate analyzed by glc. Only about 12 percent of the 3-methyl-3-buten-1-ol had been converted. The selectivity (based on the amount of 3-methyl-3-buten-1-ol converted) to 3,4-dihydro-4-methyl-2[H]-pyran was about 3 percent. 3-Methyl-2-buten-1-ol, an isomer of the starting alcohol, was present in the product mixture and was formed with a selectivity of about 51 percent.

The results of this example show that reaction temperatures, pressures, and times lower than those used in Example I tend to result in a low conversion of the starting alcohol and a significant amount of isomerization of the starting alcohol. It is currently believed that the isomerization of the alcohol is caused primarily by the low reaction pressure. Therefore, higher reaction pressures are preferred.

The disclosure, including data, illustrates the value and effectiveness of our invention. The examples, the knowledge and background of the field of the invention and of general principles of chemistry and other applicable sciences have formed the bases from which the broad descriptions of our invention including the ranges of conditions and generic groups of operant components have been developed, which then have formed the bases for our claims here appended.

We claim:

1. A process for the preparation of dihydropyrans from a $\beta$, $\gamma$-monoolefinically unsaturated alcohol wherein said unsaturated alcohol is represented by

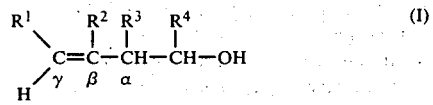

wherein each of $R^1$, $R^2$, $R^3$, and $R^4$ is individually selected from hydrogen and alkyl radicals of 1 to 6 carbon atoms per radical which process comprises reacting a $\beta,\gamma$-monoolefinically unsaturated alcohol under reaction conditions with effective amounts of hydrogen and carbon monoxide in the presence of a catalyst selected from the group consisting of the metals and carbonyl compounds of Group VIII and VIB elements, optionally on a solid support.

2. The process according to claim 1 employing about 1 to 99 mole percent hydrogen relative to the total of hydrogen and carbon monoxide, and at least about 1 mole of carbon monoxide and 1 mole of hydrogen per mole of starting unsaturated alcohol.

3. The process according to claim 4 wherein said conditions include a reaction temperature of about 0° C. to 200° C., a pressure of about atmospheric to 1000 psig, and the conducting of said reaction in a solvent.

4. The process according to claim 3 wherein said dihydropyran is represented by formula V:

and said unsaturated alcohol is represented by:

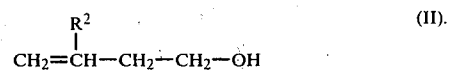

5. The process according to claim 4 wherein said dihydropyran is 3,4-dihydro-4-methyl-2[H]-pyran, and said unsaturated alcohol is 3-methyl-3-buten-1-ol.

6. The process according to claim 3 wherein said unsaturated alcohol is selected from the group consisting of 4-methyl-4-penten-2-ol, 2,3-dimethyl-3-buten-1-ol, 3-penten-1-ol, 3,4-dimethyl-4-penten-2-ol, 2-methyl-3-penten-1-ol, 3-methyl-3-buten-1-ol, 3-methylene-1-pentanol, 3-methylene-1-heptanol, and 2-methyl-3-methylene-1-pentanol.

7. The process according to claim 5 wherein said catalyst is employed on said support, wherein said support is selected from the group consisting of carbon, silica, alumina, and molecular sieve; and wherein said catalyst on a said support contains said Group VIII or VIB component to the extent of about 0.1 to 20 weight percent based on the weight of the support.

8. The process according to claim 7 wherein said Group VIII or VIB catalyst is selected from the group consisting of ruthenium, rhodium, palladium, platinum, and molybdenum, and wherein said catalyst is employed in an amount sufficient to provide about 0.01 to 10 weight ratio expressed as the element; unsaturated alcohol employed.

9. The process according to claim 7 further employing a trihydrocarbylphosphite promoter in the range of about 0.5 to 50 weight percent based on the weight of unsaturated alcohol employed.

10. The process according to claim 9 employing a mole ratio of carbon monoxide: hydrogen of about 1:1, a reaction temperature of about 40° C. to 150° C., a reaction pressure of about 75 to 300 psig, tetrahydrofuran as said solvent, said catalyst promoter is triphenylphosphite, and said catalyst is rhodium on carbon.

11. The process according to claim 10 employing as said unsaturated alcohol 3-methyl-3-buten-1-ol.

12. The process according to claim 1 further employing a recovery procedure on the reaction mixture resulting from the reaction of the unsaturated alcohol, carbon monoxide, and hydrogen, in the presence of the catalyst, wherein said recovery procedure includes cooling the resulting reaction mixture, filtering, and treating the so-obtained filtrate by fractional distillation to produce streams of solvent, if any, for recycle, unreacted unsaturated alcohol for recycle, and dihydropyran product.

13. The process according to claim 1 wherein said catalyst is the carbonyl on a solid support.

14. The process according to claim 13 wherein said catalyst is rhodium carbonyl on a solid support.

15. The process according to claim 13 wherein said carbonyl is selected from Group VIB chromium, molybdenum, and tungsten carbonyls.

16. The process according to claim 4 wherein said solvent is selected from the group consisting of glycols, saturated alcohols, aromatic hydrocarbons, and ethers.

17. The process according to claim 16 wherein said solvent is an ether.

18. A process for the preparation of dihydropyrans represented by

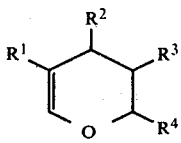

wherein each of $R^1$, $R^2$, and $R^3$, and $R^4$ is individually selected from the group consisting of hydrogen and alkyl radicals of 1 to 6 carbon atoms per radical, from $\beta,\gamma$-monoolefinically unsaturated alcohols represented by

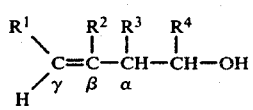

which comprises contacting a said $\beta,\gamma$-monoolefinically unsaturated alcohol under reaction conditions with effective amounts of hydrogen, carbon monoxide, and a catalyst; wherein said catalyst is selected from the metals and the carbonyl compounds of the elements of Group VIB chromium, molybdenum, and tungsten, optionally on a solid support.

19. The process according to claim 18 employing about 1 to 99 mole percent hydrogen relative to the total hydrogen and carbon monoxide, at least about 1 mole of carbon monoxide and 1 mole of hydrogen per mole of starting unsaturated alcohol, a reaction temperature of about 0° C. to 200° C., a pressure of about atmospheric to 1000 psig, and conducting said contacting reaction in a solvent selected from the group consisting of glycols, saturated alcohols, aromatic hydrocarbons, and ethers, wherein said support, where employed, is selected from the group consisting of carbon, silica, alumina, and molecular sieves, wherein said VIB component is present to the extent of about 0.1 to 20 weight percent based on the weight of said support, and employing said catalyst in an amount sufficient to provide about 0.01 to 10 weight ratio expressed as the element:unsaturated alcohol employed.

20. The process according to claim 19 wherein said unsaturated alcohol is 3-methyl-3-butene-1-ol, and said dihydropyran is 3,4-dihydro-4-methyl-2[H]- pyran.

21. The process according to claim 19 wherein said Group VIB catalyst is employed on a solid support selected from the group consisting of carbon, silica, alumina, and molecular sieves.

22. A process for the preparation of dihydropyrans represented by

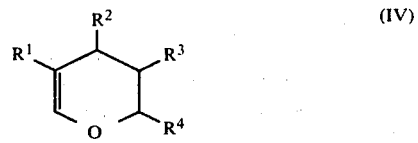

wherein each of $R^1$, $R^2$, and $R^3$, and $R^4$ is individually selected from the group consisting of hydrogen and alkyl radicals of 1 to 6 carbon atoms per radical, from $\beta,\gamma$-monoolefinically unsaturated alcohols represented by

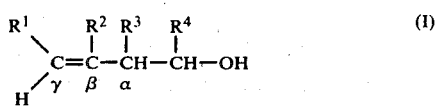

which comprises reacting a said $\beta,\gamma$-monoolefinically unsaturated alcohol under reaction conditions with effective amounts of hydrogen and carbon monoxide in the presence of effective amounts of a catalyst selected from the group consisting of the metals and carbonyl compounds of the elements Group VIII and VIB, on a solid support selected from the group consisting of carbon, silica, alumina, and molecular sieves.

* * * * *